(12) United States Patent
Jákli et al.

(10) Patent No.: US 8,056,398 B2
(45) Date of Patent: Nov. 15, 2011

(54) BROAD-RANGE NANOLITER RHEOMETER

(75) Inventors: Antal Istvan Jákli, Kent, OH (US); Christopher Allen Bailey, Beavercreek, OH (US)

(73) Assignee: Kent State University, Kent, OH (US)

( * ) Notice: Subject to any disclaimer, the term of this patent is extended or adjusted under 35 U.S.C. 154(b) by 372 days.

(21) Appl. No.: 12/378,103

(22) Filed: Feb. 11, 2009

(65) Prior Publication Data
US 2009/0255327 A1 Oct. 15, 2009

Related U.S. Application Data

(60) Provisional application No. 61/066,184, filed on Feb. 19, 2008.

(51) Int. Cl.
*G01N 11/00* (2006.01)

(52) U.S. Cl. ............................ 73/54.41; 73/64.53

(58) Field of Classification Search ............ 73/54.01, 73/54.24, 54.41
See application file for complete search history.

(56) References Cited

U.S. PATENT DOCUMENTS

| | | |
|---|---|---|
| 3,194,064 A | 7/1965 | Miles |
| 3,903,732 A | 9/1975 | Rork et al. |
| 4,571,989 A | 2/1986 | Dealy |
| 4,602,501 A | 7/1986 | Hirata |
| 4,741,200 A | 5/1988 | Hammerle |
| 4,763,512 A | 8/1988 | Taylor |
| 4,794,788 A | 1/1989 | Masters et al. |
| 5,302,878 A | 4/1994 | Soucemariandin et al. |
| 5,304,487 A | 4/1994 | Wilding et al. |
| 5,565,620 A | 10/1996 | Bohlin |
| 5,571,952 A | 11/1996 | Kauzlarich |
| 5,750,884 A | 5/1998 | Field |
| 5,885,470 A | 3/1999 | Parce et al. |
| 6,311,549 B1 | 11/2001 | Thundat et al. |
| 6,405,599 B1 | 6/2002 | Patt |
| 6,477,901 B1 | 11/2002 | Tadigadapa et al. |
| 6,484,567 B1 | 11/2002 | Hajduk et al. |
| 6,575,020 B1 * | 6/2003 | de Charmoy Grey et al. ....................... 73/54.23 |
| 6,644,101 B2 | 11/2003 | Hajduk et al. |
| 6,655,194 B2 | 12/2003 | Hajduk et al. |
| 6,668,622 B2 | 12/2003 | Hajduk et al. |
| 6,681,616 B2 | 1/2004 | Spaid et al. |
| 6,681,618 B2 | 1/2004 | Hajduk et al. |
| 6,990,851 B2 | 1/2006 | Spaid et al. |

(Continued)

OTHER PUBLICATIONS

A. Saluja et al., Measurement of Fluid Viscosity at Microlitter . . . , AAPS PharmaSciTech 2004; 5 (3) Article 47; http://www.aapsharmscitech.org.

(Continued)

*Primary Examiner* — Hezron E Williams
*Assistant Examiner* — Paul West
(74) *Attorney, Agent, or Firm* — Hudak, Shunk & Farine Co. LPA

(57) ABSTRACT

A nanoliter rheometer is capable of operating over a wide range of temperatures and permits visual observation of extremely small amounts of various often complex and/or expensive small nanoliter size fluids over a wide viscoelastic regime. The nanoliter rheometer comprises two very thin fibers, the ends of which are in close proximity to one another and desirably parallel to one another with one fiber being moved by a drive system and the remaining fiber desirably being stationary and capable of measuring a force transferred through a nanoliter size fluid located between the two fibers ends. The transferred force can be measured either by an LCR meter or a piezoelectric crystal and recorded as by a lock-in amplifier.

16 Claims, 12 Drawing Sheets

U.S. PATENT DOCUMENTS

| | | | |
|---|---|---|---|
| 7,040,144 | B2 | 5/2006 | Spaid et al. |
| 7,047,794 | B2 | 5/2006 | Hajduk et al. |
| 7,051,581 | B2 | 5/2006 | Mansky et al. |
| 7,059,176 | B2 | 6/2006 | Sparks |
| 7,188,515 | B2 | 3/2007 | Burns et al. |
| 7,210,332 | B2 | 5/2007 | Kolosov et al. |

OTHER PUBLICATIONS

N. Srivastava, et al., Nanoliter Viscometer for Analyzing Blood Plasma . . . , Anal. Chem. 2005, vol. 77, pp. 383-392, ACS, published on web Dec. 7, 2004.

Z. Han et al., A PDMS Viscometer for Microliter Newtonian fluid, J Micromech, Microeng., 2007, vol. 17, pp. 1828-1834, 2007 IOP Publishing Ltd, UK.

A. Jakli, et al., Rheology of a Pyramidal Liquid Crystal, Liquid Crystals, 1999, Vo. 26, No. 7, pp. 945-952, Taylor & Francis Ltd.

Y. Hou, et al., Instrument Techniques for Rheometry, Review of Scientific Instruments, vol. 76, pp. 101101-1-101101-19, American Institute of Physics, 2005.

N. Srivastava et al., Electronic Drop Sensing in Microfluidic devices . . . , Lab Chip, 2006, vol. 6, pp. 744-751, The Royal Society of Chemistry.

A. Agoston, et al., Evaluation of a Vibrating Micromachined Cantilever . . . , Sensors and Actuators A, 2005, 123-124, pp. 82-86, Elsevier B.V.

B. Mert, et al., A New Method to Determine Viscosity . . . , Rheol. Acta., 2003, vol. 42, pp. 534-543, Springer-Verlag.

A.G. Chmielewski et al., Rheological Properties of some Biopheny . . . , Rheol Acta., 1984, vol. 23, pp. 207-210.

N. Willenbacher, et al., Broad Bandwidth Optical and Mechanical . . . , Phys Review Letters, 2007, PRL, vol. 99, pp. 068302-1-068302-4, The American Physical Society.

\* cited by examiner

US 8,056,398 B2

BROAD-RANGE NANOLITER RHEOMETER

CROSS REFERENCE

This patent application claims the benefit and priority of U.S. provisional application 61/066,184, filed Feb. 19, 2008 for BROAD-RANGE NANOLITER RHEOMETER, which is hereby fully incorporated by reference.

The U.S. Government may have certain rights in this invention under the National Science Foundation FRG under Contract No. DMS-0456221.

FIELD OF THE INVENTION

The present invention relates to a nanoliter rheometer that can measure over a wide viscoelastic regime very small amounts, e.g. nanoliters, of fluids over a broad temperature range, and also allow optical observation thereof as through a microscope. The fluids can be expensive, complex, or available in scarce amounts.

BACKGROUND OF THE INVENTION

Rheological studies have been found useful in several important arenas from medical diagnostics and biological sciences of cellular and tissue functions, to manufacturing of inks, paints and varnishes, and to better understand basic non-Newtonian materials such as polymers and liquid crystalline materials. However, some of these fields rely on a limited amount of material, especially in the biological fields (typically on the order of a few mL). Therefore, recent technological needs have driven a renewed interest in both shrinking the scale of rheological techniques and the amount of material needed to perform such measurements.

Classical rheological equipment can be generalized into three basic categories that utilize capillary, rotational, or falling/rolling ball techniques. While some success has been made in the shrinking the size scale of the latter two, they still rely on amounts of material on the order of a mL. Much more successful attempts have been made in shrinking the capillary methods, mainly due to the successes of micro-fabrication techniques in creating micro-fluidic channels. These methods have reported successful viscosity measurements using material volumes in the order of a μL down to about twenty nL. However these methods are typically valid for Newtonian flow regimes and low viscosities that in general limit their usage as a general Theological tool. Some improvements on this technique have allowed greater viscosity range ($1cP<\eta<100$ cP), but is still limited to Newtonian behavior. Many classical rheometers used to measure complex viscoelastic properties relied on oscillatory motion to induce shear stresses on a fluid. This technique has been applied to several micro-viscometer techniques based on resonance properties of cantilevers or piezoelectric crystals. Although many of these techniques rely on being submerged in a container of material, one method using quartz crystals could measure rheological properties of around 10 μL of material. This method, however, resonated between 5-10 MHz, resulting in very large shear rates, usually well above typical non-Newtonian behavior transitions.

In summary, although there have been numerous attempts at developing rheometers capable of measuring material properties with very small volumes, there has not yet been one flexible enough to perform generalized measurements over a wide range of material types, viscoelastic regimes, and broad temperature ranges.

SUMMARY OF THE INVENTION

A nanoliter rheometer is designed to permit viscosity and elasticity measurements over a wide range utilizing very small size amounts of fluids such as nanosize fluids as small as about 5 or 10 nanoliters. The rheometer is well suited for analyzing scarce or rare, expensive, or complex fluids such as liquid crystals including those containing nano particles, soft biological materials that are often scarce such as DNA solutions, protein solutions, living cells, and the like. An advantage of the nanoliter rheometer is the existence of an optical or visual viewing area or window that permits direct observation of the viscosity or elastic measurements via a naked eye or more desirably through a microscope. The nanoliter rheometer contains two thin fibers the ends of which are in close proximity and substantially parallel to one another. In an alternative embodiment, the nanoliter rheometer contains two thin fibers the ends of which have a common axis with a gap existing between the two ends. One fiber is substantially stationary and the remaining fiber is set forth in motion through a drive system that can be a variety of different mechanical, electrical, or other devices including transducers such as a speaker that transforms electrical energy into mechanical movements. A transferred force measurement device such as a LCR meter or a piezoelectric crystal produces electrical outputs that can be recorded for analysis with respect to the viscosity and elastistic properties of a nanoliter size fluid placed between and contacting the ends of the motion fiber and the stationary fiber.

In general, a nanoliter rheometer, comprises: a thin motion fiber and a thin substantially stationary fiber, the ends of said motion fiber and said stationary fiber being in close proximity and substantially parallel to each other; or the ends of said motion fiber and said stationary fiber generally have a common axis; said ends of said motion fiber and said substantially stationary fiber capable of retaining a small nanoliter sized fluid therebetween; a drive system connected to and for imparting motion to said motion fiber; and a transferred force measurement device connected to said stationary fiber and capable of measuring the force imparted to said substantially stationary fiber by said motion fiber through said fluid.

BRIEF DESCRIPTION OF THE DRAWINGS

FIG. 2a is a partial top view showing the ends of the stationary fiber and the movement fiber with a droplet of a fluid there between;

FIG. 2b is a partial top view of the same fiber ends and a droplet showing the important parameters of the width D of the fiber, the center w (width) of the droplet between the fibers, the displacement amplitude s of the motion fiber, and the distance $L_o$ between the fibers, that are utilized to measure and calculate the shear stress;

DETAILED DESCRIPTION OF THE INVENTION

Figure 1:
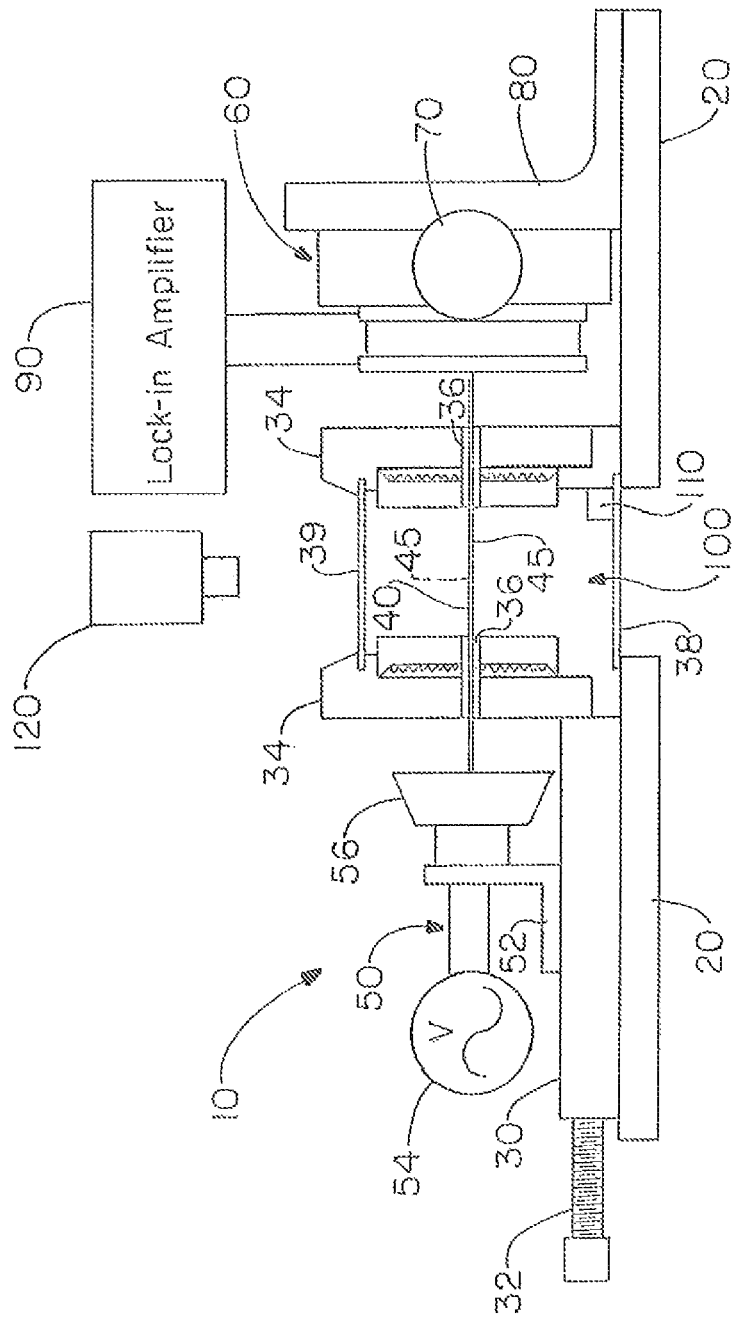
FIG. 1 is a side elevation view that diagramatically illustrates a nanoliter rheometer of the present invention comprising three basic components, a drive system such as a speaker (left), a temperature controlled chamber (center), and a piezoelectric crystal to measure a transferred force (right)

While an embodiment of a nanoliter rheometer according to the present invention is shown in FIG. 1, it is to be understood that variations thereof and other embodiments can also be utilized within the concepts of the invention. Nanoliter rheometer 10 contains a base or substrate 20 and can be made out of any suitable material such as wood, plastic, metal, or the like. Positioning block 30 contains an adjustment screw 32 that is connected to drive system support 52 of drive system 50 so that upon rotation of screw 32, the speaker system can be moved laterally to the left or right as set forth in FIG. 1, or in other words, along an X axis. Position block 30 is fastened to base 20 in any conventional manner such as by fasteners, glue, or the like.

Rheometer 10 contains a plurality of upright side walls 34, that can be made out of any conventional material such as metal or plastic and can contain insulation therein, and forms a volume or chamber 100 of any desired shape such as a cube, cylinder, or the like. Apertures 36 exist within side walls 34 that permit a very small size fiber to extend therethrough. Motion fiber 40 is connected to drive system 50 and substantially stationary fiber 45 is connected to transferred force measurement device 60. By the term "substantially stationary" it is meant that fiber 45 can generally reciprocate along an X axis with respect to motion imparted thereto through fluid 60 and fiber 40 but that the extent of motion of fiber 45 along an X axis is only 10% or less of that of total movement length of motion fiber 40 and desirably 1% or less. However, it is highly preferred that fiber 45 is stationary and hence subsequently herein will be referred to a stationary fiber although, as noted, it can have a small reciprocal movement along an X axis.

Drive system 50 comprises in addition to drive support 52 an electrical voltage source 54 that is connected to a motion device such as speaker 56. It is to be understood that drive system 50 can comprise numerous different types of transducers whereby an electrical current, a motor, or the like is attached to motion fiber 40 to cause it to oscillate, reciprocate, or otherwise move in any desired manner and that the amplitude and frequency of the fiber end can be controlled. For example, voltage source 54 can convey a sinusoidal signal or other type of periodical motion to speaker 56 such that the lateral motion of motion fiber 40 moves in a sinusoidal pattern along the X axis. The displacement "s" distance of the motion fiber is generally from about 1 to about 200, desirably from about 10 to about 100, and preferably from about 20 to about 70 microns.

Figure 2:
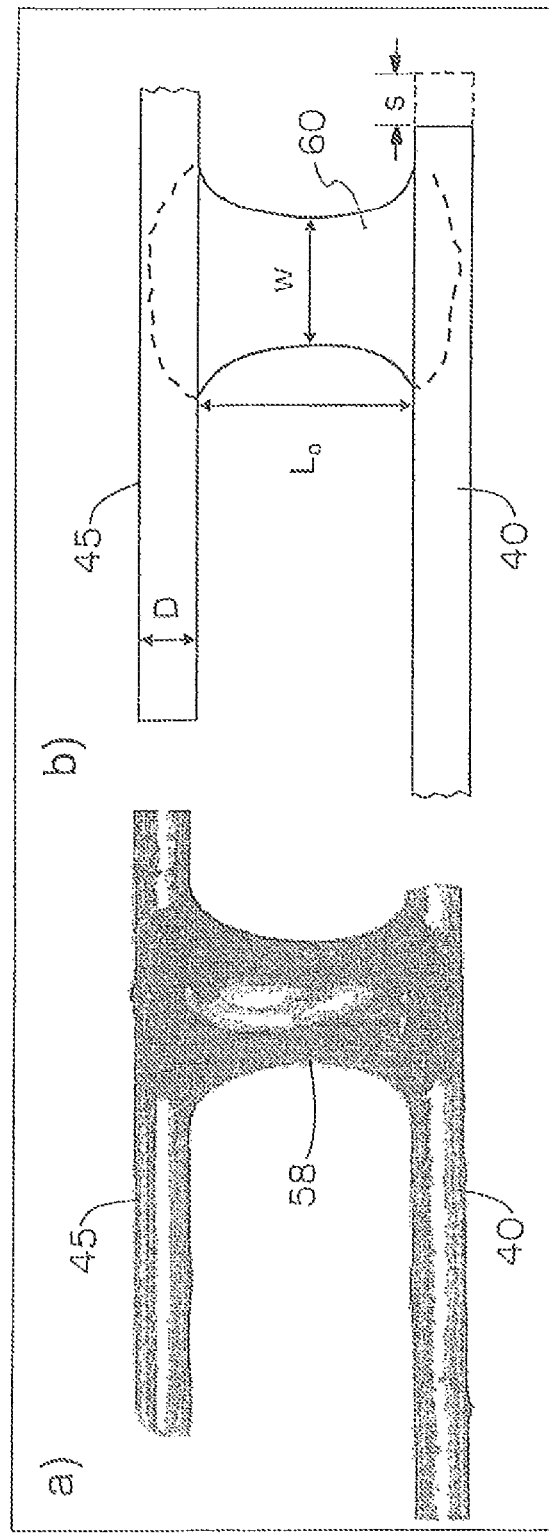
Figure 4:
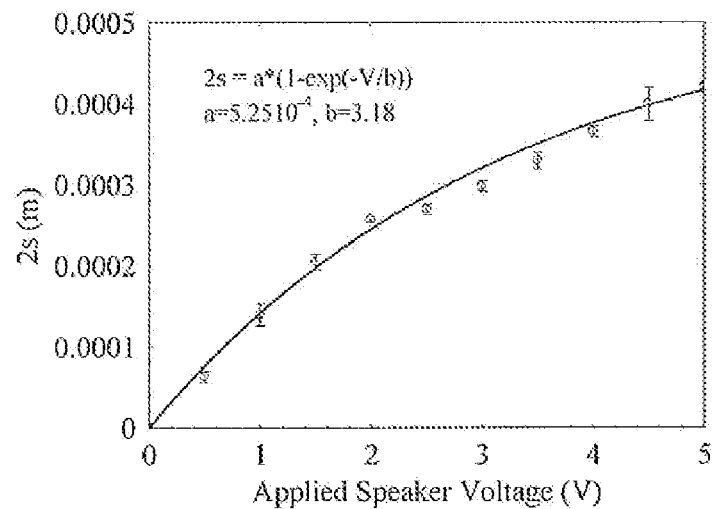
FIG. 4 shows a) Displacement versus Voltage at 130 Hz and b) the displacement per volts versus frequency in the small voltage regime along with their best fit behavior. The amplitude dependence follows an exponential saturation behavior while the frequency dependence for small voltages follows a combination of behaviors due to a natural time scale relationship (LR circuit) and resonance behavior (LRC behavior)
Figure 4:
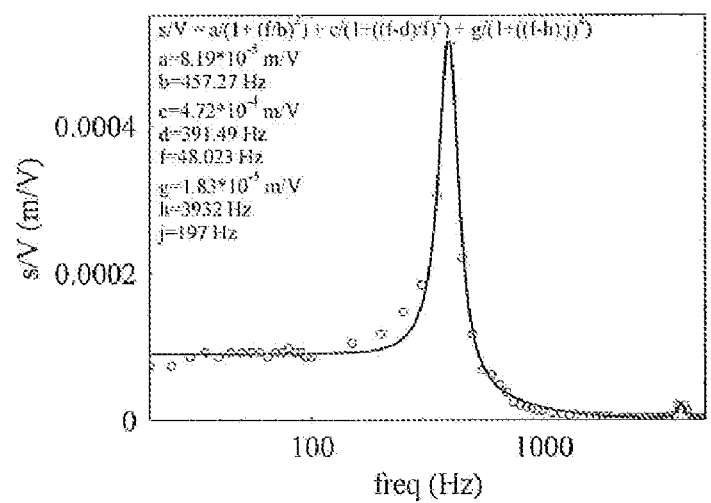

Although not shown, speaker support 50 can be attached to another adjustment screw or system that adjusts the location of motion fiber 40 upward or downward in the drawing of FIGS. 1 and 2, or along a Y axis with respect to stationary fiber 45. Still further, and not shown, another adjustment screw or other means can be attached to drive system support 52 so that motion fiber 40 is moved either behind or forward of the plane of FIG. 1, that is along a Z axis. In summary, any apparatus or set-up can be utilized to adjust the location of fiber 40 in an X, Y, or Z direction, or any combination thereof with respect to fiber 45. While any relationship of motion fiber 40 with respect to stationary fiber 45 can be utilized to locate the ends of each fiber in proximity to one another and in an overlapped manner, (i.e. Y (up) and/or Z (behind) direction), desirably, the end of one fiber (e.g. the stationary fiber) can be horizontally located behind the motion fiber (that is in the Z direction). Thus, through adjustment of motion fiber 40 along the Y axis, the distance between the surface of the parallel fibers can be adjusted to a desired length $L_o$, see FIG. 2. The surface distance between the two fibers is generally from about 10 microns to about 1 mm and desirably from about 1 micron to about 200 microns. As shown in FIG. 2, a small droplet of fluid 58 can be placed between the two fiber ends and the fluid will be held in place by capillary action between motion fiber end 40 and stationary fiber end 45. Depending upon the input of drive system 50, the amount of oscillation of motion fiber 40 can be controlled.

Figure 3:
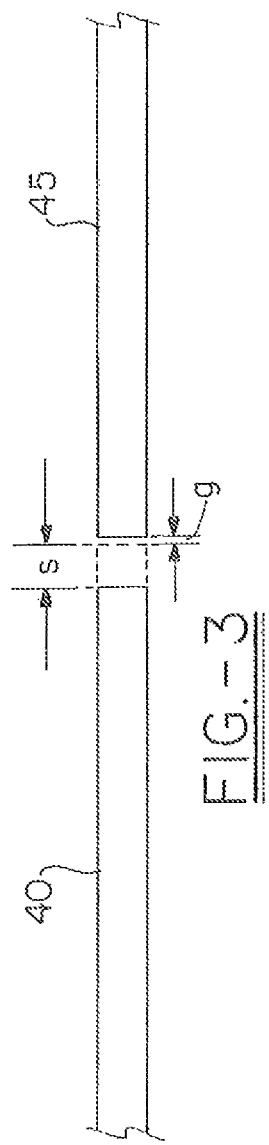
FIG. 3 is partial view of two fibers that are located on a common axis wherein "s" is a displacement amplitude of motion fiber and "g" is a gap between the stationary fiber and the closest distance of the motion fiber.

An alternative embodiment is shown in FIG. 3 wherein the motion fiber and the stationary fiber are located along a common axis. That is, the two fibers have a center line that is generally along an X axis with very little or no offset radius from the center line as in an Y and/or Z direction. If offset, the radius distance thereof is very little such as from about 10 or less and desirably from about 1 or less microns. As shown in FIG. 3, displacement distance "s" of the motion fiber is the same as set forth above (i.e. from about 1 to about 200, desirably from about 10 to about 100, and preferably from about 20 to about 70 microns). The remaining distance between the end of the motion fiber and the stationary fiber is gap distance "g" that generally can range from about 1 to about 100, desirably from about 10 to about 75, and preferably from about 20 to about 50 microns with regard to the closest displacement distance of the motion fiber to the stationary fiber. The location of the motion fiber and the stationary fiber along a common axis is desired whenever the measurement of an extensional viscosity is desired as with respect to polymers and polymer solutions.

The force imparted to oscillating fiber 40 will be transferred to stationary fiber 45 through fluid 58 transferred force measurement device 60 can measure the amount of transferred force in any conventional manner. For example, the transferred force can be converted into an electrical current such as through piezoelectric crystal 70 that can be attached or fastened to upright support 80 fastened in any conventional manner to base 20. In order to record the oscillating transferred force that is generally phase dependent, any conventional lock-in amplifier 90 can be utilized, that desirably also filters out noise. In summary, the nanoliter rheometer measures the output force through stationary fiber 45 and then calculates the difference from the input force to determine the viscosity and elasticity of a particular fluid.

The present invention can be utilized to analyze numerous different types of fluids having a nanoliter volume with the individual fluids varying greatly in viscosity and elasticity. Since the distance between the overlapped ends of motion fiber 40 and stationary fiber 45 can be adjusted in generally any direction to insure sufficient capillary action, contact of the fluid with both fibers ends can be readily maintained during testing thereof. A wide range of volumes of various fluids can be analyzed by the present invention such as generally volumes of from about 5 to about 200 nanoliters, desirably from about 10 to about 100 nanoliters and often preferably from about 10 to about 50 nanoliters.

Another distinct advantage of the present invention is that the viscosity and elasticity measurements of the fluid can be obtained over a wide range of temperatures since chamber 100 containing the ends of motion fiber 40 and stationary fiber 45 therein is desirably substantially enclosed and preferably entirely enclosed. That is, temperature controlled chamber 100 within the rheometer as general defined by sidewalls 34, front and back walls (not shown), bottom plate 38, and top plate 39 that can be a window, can be heated and maintained at a predetermined temperature in any general manner such as through electrical heating element 110. Thus, the viscosity and elasticity values of a particular fluid 60 can be determined over a wide range of temperatures.

Another advantage of the present invention is that the testing procedure can be viewed through top plate 39 which preferably is transparent such as a glass window by either the naked eye, or preferably through the use of an optical magnifying device such as microscope 120.

The fibers of the nanoliter rheometer of the present invention are desirably partly flexible in order to dampen any perpendicular, or forward-backward, or any combination thereof, vibrations with respect to the fiber and thus generally measure only output forces in the X direction. A preferred rheometer uses glass rods that have a bending stiffness of at least about ~30 N/m, however it need be only stronger than the fluid surface tension, e.g. ~20 mN/m, so that the rods can be separated. The input and output (motion and stationary) fibers can be generally made of any material such as plastic, non-metal, glass, or metal, or any combination thereof, and while they can be conductive, desirably they are not. The plastics can be a thermoset or thermoplastic so long as they do not soften at the operating temperature of the rheometer. Examples of suitable plastics include polyesters, polycarbonates, polyamides or nylons, polyimides, polyurethanes, phenolic resins, polyolefins such as polyethylene and polypropylene, polystyrene, polyvinyl chloride, and the like, as well as combinations thereof. Non-plastic fibers can also be utilized such as non-metals such as boron, carbon, metal, and the like, as well as combinations thereof. Examples of metals include steel, aluminum, copper, brass, titanium, and the like including combinations thereof. Glass fibers include known and conventional types of glass including sodium glass, E glass, and the like. Although hollow fibers can be utilized, they are generally not desired or preferred. Generally any cross-sectional shape of the fiber can be utilized such as square, rectangular, a polygonal, circular, in the shape of a gear having grooves or ridges around the periphery thereof, and the like, with a circular cross-sectional area being preferred.

An important aspect of the present invention is that the diameter, that is the longest cross-sectional length regardless of the shape (e.g. square, oval, circular, etc.), of the fiber is small and generally ranges from about 50 microns to about 1 mm, desirably from about 100 microns to about 500 microns and preferably from about 100 microns to about 200 microns.

Fluid 58 can be either Newtonian or non-Newtonian. While liquids are generally utilized, regardless of their viscosity, solids that melt and are liquids at the operating temperature of the nanoliter rheometer can also be utilized. The number and type of fluids are vast and include such types such as liquid crystals, biological substances, elastomers, gels, polymer solutions, polymers, colloidal suspensions, foams, fluid mixtures, nanoparticles solutions, and the like.

An advantage of the present invention is that only very small amounts of expensive, scarce, rare, hard to obtain, etc. fluids are required in order to obtain the viscosity and elasticity thereof over a wide range of temperatures. Moreover, the present invention allows optical observation of the test operation.

The nanoliter rheometer of the present invention is thus very versatile with regard to the type, temperature ranges, etc, of the fluids, and can be readily customized to test particular types of fluids by varying the thickness of the fiber, varying the drive system input as with regard to amplitude and frequency thereof, as well as obtaining lag time output by varying the distance between the fibers, and the like. The amplitude or reciprocation of input fiber or motion fiber 40 in the X direction as previously noted can vary from about 1 to about 200 microns and desirably from about 10 μm to about 100 microns. The frequency thereof can generally be from about 1 Hz to about 5 kHz. The reciprocation or oscillation movement of the end of fiber 40 can follow any desired pattern such as a sinusoidal wave, triangular, rectangular, and the like. As also shown in FIG. 2, the fibers are preferably parallel to one another although it is within the scope of the present invention that they can be substantially parallel, that is they can diverge from one another at an angle of from about 0.1° or less, desirably about 0.01° or less, and as noted preferably are parallel.

The actual nanoliter rheometer design and calibration will now be set forth as well as to the calculation of the LCR measurements, piezoelectric measurements, optical measurements, and the like.

Briefly, FIG. 1 is a sketch that shows the three major components of the device, a drive system 50 such as speaker 56 (left), a temperature controlled chamber 100 (center), and transferred force measurement device 60 such as lock-in amplifier 90 and piezoelectric crystal 70 to measure the force (right). Measurements are obtained by driving the speaker at a particular frequency which oscillates motion fiber 40. The force of the oscillating fiber is transferred to stationary fiber 45 by fluid 58 (FIG. 2) that is placed between the two fibers. The transferred force is measured as current via a piezoelectric crystal and recorded using a lock-in amplifier at whichever harmonic of the input signal is desired (typically 1$^{st}$ harmonic).

The center component, as noted, is temperature controlled chamber 100 where the sample is placed between the two fibers 40 and 45. Many different fiber types can be utilized as noted above such as optical fibers since they are not thermally or electrically conductive or chemically reactive, and because they allow flexibility for smooth driving and they can be formed to a very controlled shape. The right side of FIG. 1 discloses a sensing device, for example piezotransducer 70, that converts the mechanic force to an electric signal.

Two basic measurement techniques are possible with the above setup. The first one is obtained by using a lock-in amplifier 80 attached to the piezoelectric crystal as set forth in FIG. 1 to measure the force transferred from the drive system through the fluid; the second as set forth hereinbelow in more detail relies on using a LCR (Inductance Capacitance Resistance) meter to measure the shift of the resonance frequency of the driving device due to changes in the impedance. Both of these viscosity calculation systems are known to the art and to the literature and thus will be briefly explained herein below.

FIG. 2 shows the image of a fluid droplet 58 through an inverted microscope between the two optical fibers (125 microns diameter). Also included is a diagram of the droplet showing the experimental parameters used in the calculation of the shear stress.

FIG. 2a shows a droplet 58 of a liquid crystal, namely pentyl cyano biphenyl (5CB) (~12 nL) at 45° C. between two D=125 micron diameter optical fibers as viewed through an inverted microscope BX40. FIG. 2b is a diagram of the same droplet along with important parameters (D is the diameter of the fibers, w is the center width (waist) of the droplet between the fibers, s is the displacement amplitude of speaker 56, and L is the distance between the fibers) that must be measured to calculate the shear stress.

The diameter of the fiber is D=125 micron and is used as the scale in many of the measurements. The droplet waist is w, the distance between the fibers is L, and oscillation amplitude is s. As the material somewhat overlaps the optical fiber, the effective length L of the fluid material under test will be larger than $L_o$ (L=$L_o$+δ). In general δ and must be a fitting parameter; however it is known that δ is between zero and the radius of the fiber. These parameters can be used to estimate the effective cross sectional area A and droplet volume V as $$A \approx \pi/4 wD = \pi r^2 \text{ and } V \approx AL \text{ for large Length} \quad (1)$$

Measurements of the voltage and frequency dependencies of s are needed to correctly characterize the strain behavior. Examples of these graphs are shown in FIGS. 4-14.

The voltage dependence of the speaker amplitude arises from the competition of electric and elastic forces on the speaker head, which is also frequency dependent, making the calibration difficult. The resonant behavior of the frequency dependence makes it difficult to measure the stresses using lock-in techniques near resonance. Therefore the focus will be on two types of measurement techniques. The first technique measures changes of the speaker resonance due to the presence of the fluid using frequency sweeps and an LCR meter, and the second method uses the piezoelectric crystal at relatively low frequency (130 Hz in the examples shown below) with voltage and temperature sweeps, and the other uses low voltage (<0.1V).

LCR Measurements

This method does not use the piezo-transducer of the instrument and relies only on the sensitivity of resonant behavior to changes in property values. An LCR meter is utilized along with circuit analysis to determine the viscous and elastic behavior for these materials. The methods for determining these properties will be discussed separately because they are determined by different components of the circuit analysis.

Viscosity Determination

The basic theory of this model relies on the fact that at resonance all of the electric power is being dissipated. Therefore assuming that changes in resonance can be caused by the presence of the fluid, than one can be able to measure the extra power being dissipated by that fluid and calculate the viscosity η. This equation takes the following form, $$P_f(\omega_{rf}) - P_o(\omega_{ro}) = Q(\omega_{rf}) \quad (2)$$

where the subscripts f and o in the resonance frequency ($\omega_{rf}$ and $\omega_{ro}$) represent the setup with or without the fluid, respectively. If one uses the dissipation factor $Q(\omega) = \eta A \omega^2 / L_o s^2$, which has units of Watts, the form of the electric power $P = v^2/R$ (where R is the electric resistance and V is the applied voltage), and the assumption that the displacement s is proportional to the voltage for small voltages (see FIG. 4b) then one can obtain the following relationship for the viscosity which is related to the change in the resistance of the drive system.

$$\frac{1}{2}\left(\frac{1}{R_f} - \frac{1}{R_o}\right) = \eta A \frac{\omega^2}{L_o} \left(\frac{s}{V}\right)^2 \quad (3)$$

The extra factor of two comes from the fact that the voltage used in these calculations must be converted to RMS (root mean square) to correctly calculate the power, and L has reduced to $L_o$ because it appears that δ becomes negligible at these higher strain rates.

Elasticity Measurement

As in the measurements for viscosity, the approach for elasticity can be a similar way. If the average power (rate of change of energy averaged over one period T) of a spring system with spring constant k and oscillatory displacement is $x(\omega) = se^{i\omega t}$, the following is obtained.

$$\langle P \rangle_T = \frac{d}{dt}\left(\frac{1}{2}kx^2\right) \approx i\omega k \left(\frac{s}{V}\right)^2 V^2 \quad (4)$$

What is interesting about equation (4), is that if it is assumed that the displacement is proportional to the voltage then the inverse of the effective impedance is $$\frac{1}{2Z} = \frac{1}{2}i\omega\left(2k\left(\frac{s}{V}\right)^2\right) = \frac{1}{2}i\omega C_e \quad (5)$$

which is identical to a capacitance due to elasticity $C_e$. Therefore the elastic constant k due to a fluid element can be calculated in a similar manner as done for the dissipation in equation (3, resulting in the following relationship.

$$(C_e - C_0) = 2k\left(\frac{s}{V}\right)^2 \quad (6)$$

Where $C_o$ is the capacitance measured without the fluid material.

Therefore shifts in capacitance can be explained by changes of elasticity of the system. This is less accurate than the viscous term because of the elasticity of the speaker membrane also plays a significant role, which in many cases will be larger than the capacitances due to fluid elasticity, therefore placing the percent changes of the capacitance due to the fluid element below the resolution of the LCR meter (0.1% of reading), which could not be detected for the 5CB sample with our current device.

Circuit Model

Figure 5:
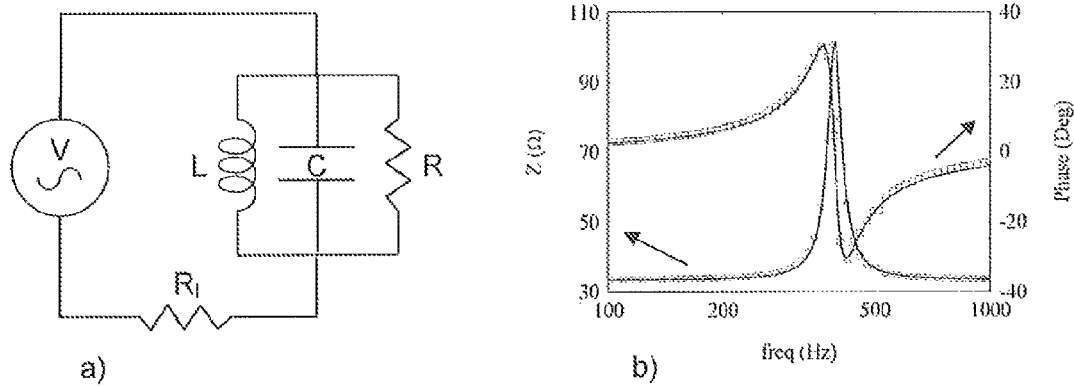
FIG. 5 shows a) The approximate LCR circuit model for the speaker. b) The measured impendence and phase vs. frequency for the speaker with no fluid at 45° C. along with fit using the circuit approximation.

The resonance behavior comes into play from the fact that the LCR meter only calculates the impedance of the speaker which holds both phase and magnitude information in its value. Therefore, if an appropriate electrical model for our speaker system exists, then one is able to calculate the dissipative resistance R related to the frictional losses in the system. The effective electric circuit that we used to describe the speaker and the fit of this model to the measured data is shown in FIG. 5.

Figure 6:
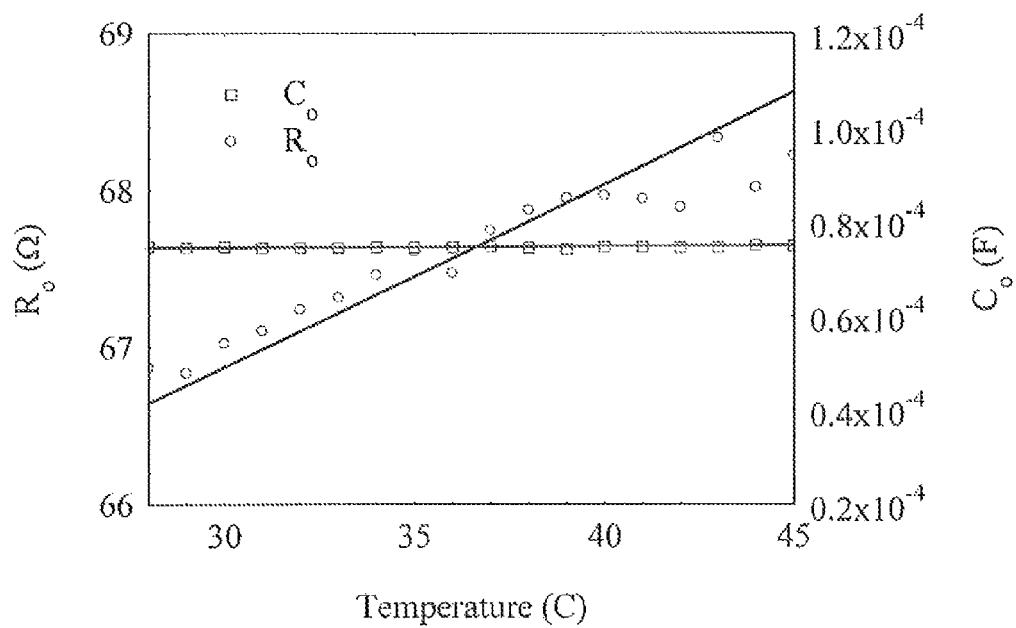
FIG. 6 shows temperature dependence of the empty resistance $R_o$ and $C_o$ along with their best fit curves.
Figure 7:
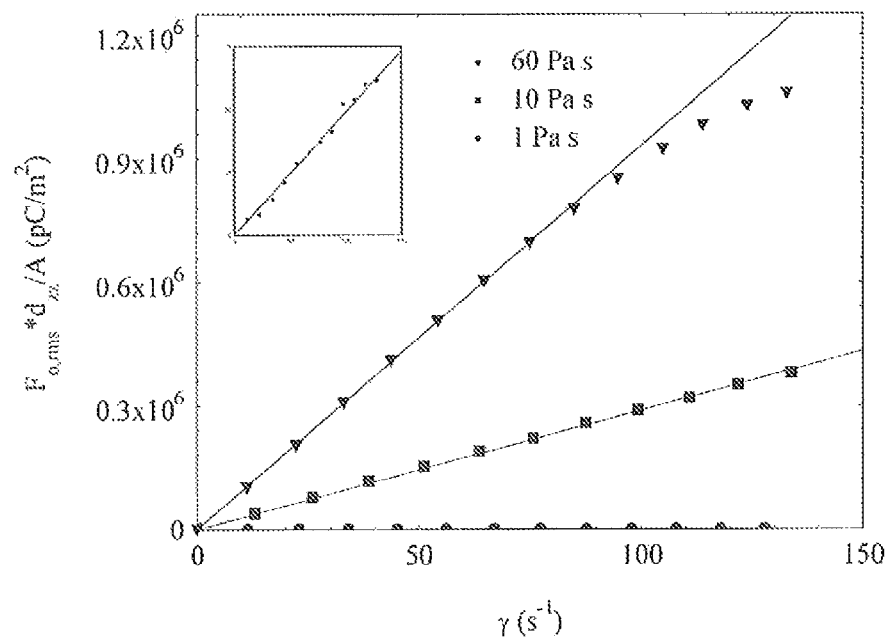
FIG. 7 shows the measured charge density versus the shear rate for three fluids with of known viscosity (castor oil (1 Pas) and two silicone fluids (10 and 60 Pas) from Clearco. The fit of these plots represents the effective piezoelectric coefficient giving a value of 160 pC/N.

The equation used in the fit of the magnitude $|Z(\omega)|$ and phases $\psi$ are shown below $$|Z(\omega)| = \sqrt{\left(R_l + \frac{R}{1+\left(\frac{\omega}{\omega_1} - \frac{\omega_2}{\omega}\right)^2}\right)^2 + \left(\frac{R\left(\frac{\omega_2}{\omega} - \frac{\omega}{\omega_1}\right)}{1+\left(\frac{\omega}{\omega_1} - \frac{\omega_2}{\omega}\right)^2}\right)^2} \quad (7)$$

$$\psi(\omega) = \tan^{-1}\left(\frac{\left(\frac{\omega_2}{\omega} - \frac{\omega}{\omega_1}\right)}{1+\frac{R_l}{R}\left(1 + \frac{\omega}{\omega_1} - \frac{\omega_2}{\omega}\right)}\right) \quad (8)$$

Where R is the resistance, $R_l$ is the lead resistance, $$\omega_1 = \frac{1}{RC},$$

and $$\omega_2 = \frac{R}{L}$$

are the characteristic angular frequencies. It is also important to note that the resonance frequency, $$\omega_r = \sqrt{\omega_1 \omega_2} = \frac{1}{\sqrt{LC}},$$

is determined by the geometric mean of these two natural frequencies. FIG. 6 shows the temperature dependence of the empty resistance $R_o$ between 25° C. and 45° C.

Then by using (3), it can be determined the viscosity as a function of temperature by determining the values of R and $\omega_r$ for the sample at each temperature.

Although this method gives excellent results at the resonance frequency, it does not allow measurement as the function of frequency (thus to probe the viscoelastic behavior). For this reason the piezoelectric measurements have been explored.

Piezoelectric Measurements

This method uses a piezoelectric crystal attached to the still glass fiber to measure the charges (current) induced by forces applied to the glass fiber. Coupled to a lock-in amplifier it can allow force measurements with the sensitivity related to the sensitivity of the lock-in current (~100 fA), in our case this sensitivity is dependent on the frequency used ~1 μN @ 130 Hz. The strength of such a measurement is that the resolution is a function of the several physical parameters that can be controlled experimentally allowing the flexibility to measure the fluid properties over many orders of magnitude (we have done between 0.01 Pa*s to 100 Pa*s but are not limited to this range). For the calibration of the measurements the piezoelectric coupling constant ($d_{zz}$=160 pC/N) was determined by measuring oils with known viscosity at low shear rates and determining the ratio ($1/\omega^2/A$) which should be the viscosity multiplied by the piezoelectric coupling constant.

Basic Theory and Results

From Newton's second law for the measured force, F can be written as $$F = GA\epsilon + m_{eff}L\ddot{\epsilon} + \eta A\dot{\epsilon} \quad (9)$$

In this expression $\epsilon$ is the shear strain, $\dot{\epsilon}$ is the shear rate, and $\ddot{\epsilon}$ is the shear acceleration. The first term on the right hand side is the kinetic energy of the material, and the second term combines the potential energies from elasticity (G is the elastic shear modulus), and the third term describes the shear force due to viscosity $\eta$.

With the assumptions that the cross sectional area A is constant and using the following relationships for periodic force $F = F_o e^{i\omega t}$ and strain $\epsilon = s/L e^{i\omega t}$, and defining an effective mass ($m_{eff}$) which is decoupled with a phase shift of $\phi_1$ from the elastic stress to account for device vibrations, we can obtain the force relationship shown below.

$$|F_o| = \sqrt{\left(GA\left(\frac{s}{L}\right) + (m_{eff}\omega^2 s)\cos\phi_1\right)^2 + \left(\frac{\eta}{2}A\left(\frac{\omega s}{L}\right) + (m_{eff}\omega^2 s)\sin\phi_1\right)^2} \quad (10)$$

In this solution, it is noted that the force $F_o$ has two components out of phase of each other by 90°. However by taking measurements of the shear stress ($\tau = F/A$) versus L in the isotropic phase (G=0) one can calibrate for the effective mass ($m_{eff}$=0.35 mg) and the associated shifts in phase ($\phi_1$=6°). The equations for the magnitude of the elastic stress $\tau_{elast}$ and viscous stress $\tau_{visc}$ and the phase $\phi_1$ then take the following forms.

$$\tau_{elast} = \left(\frac{m_{eff}\omega^2 s}{A}\right)\cos\phi_1 \quad (11)$$

$$\tau_{visc} = \frac{\eta}{2}\left(\frac{\omega s}{L}\right) + \left(\frac{m_{eff}\omega^2 s}{A}\right)\sin\phi_1 \quad (12)$$

There also exists a constant phase shift $\phi_0$, which is related to the lag of the speaker to the applied voltage and is for this device, 75°. By using this notation, one can now determine G and $\eta$ by measuring the magnitude and phase of the force, the geometrical parameters of the droplet, and the voltage dependence and frequency of the applied displacement, as $$G = \left(\frac{L}{As}\right)(F_o\cos(\phi - \phi_0) - (m_{\mathit{eff}}\omega^2 s)\cos\phi_1) \quad (13)$$

$$\eta = \left(\frac{L}{A\omega s}\right)(F_o\sin(\phi - \phi_0) - (m_{\mathit{eff}}\omega^2 s)\sin\phi_1) \quad (14)$$

Figure 8:
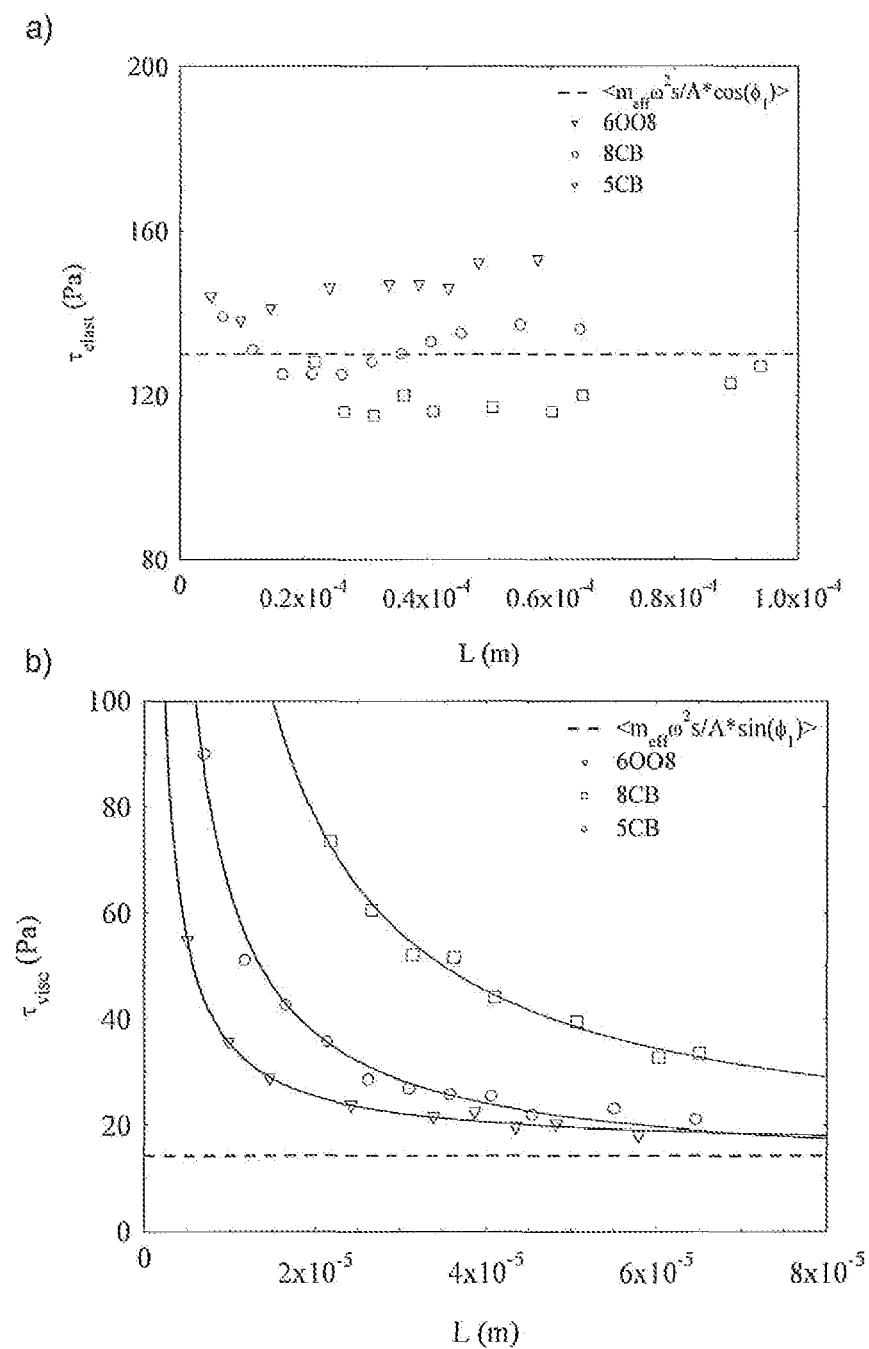
FIG. 8 shows the L dependence of the elastic (a) and viscous (b) stresses along with their theoretical fits for several nematic materials in their isotropic phase. The resulting values for the average magnitude and phase of the inertial force can be used to calculate the effective mass ($m_{eff}$=0.36±0.04 mg) and inertial phase shift ($\phi_1$=6±1°)

Equation (11)-(12) can be seen best in the fit to measure data in FIG. 8 for the liquid crystal 5CB, see Table 1, at 45° C. (note that it is assumed that G=O because this is in the isotropic phase).

Figure 9:
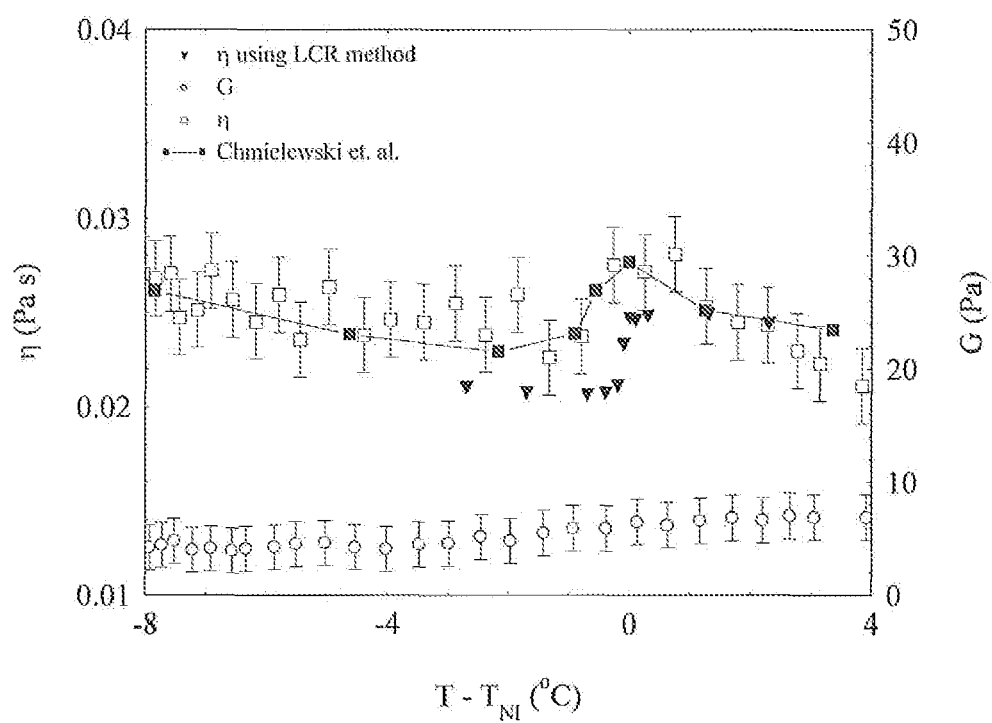
FIG. 9 show viscosity measurements of 5CB as a function of reduced temperature as compared to the values measured by Chmielewski et al. using a classical rotational viscometer. One finds that all curves agree within 2 cP and are around typical values cited for 5CB.

The measured temperature dependences of the viscosity $\eta$ and elastic constant G determined from the resonance measurements and by the piezoelectric technique are shown in FIG. 9. For comparison also included is the viscosity measured by Chmielewski et al. on non-aligned 5CB using a Rheotest 2 viscometer with two-gap coaxial cylinders containing about 1 ml material. One can see very good agreement is within 2 cP error, in spite of the fact that one used 5 orders of magnitude less materials. The value of G is small and is most likely related to minute changes between the fibers, air, and liquid interface.

Figure 10:
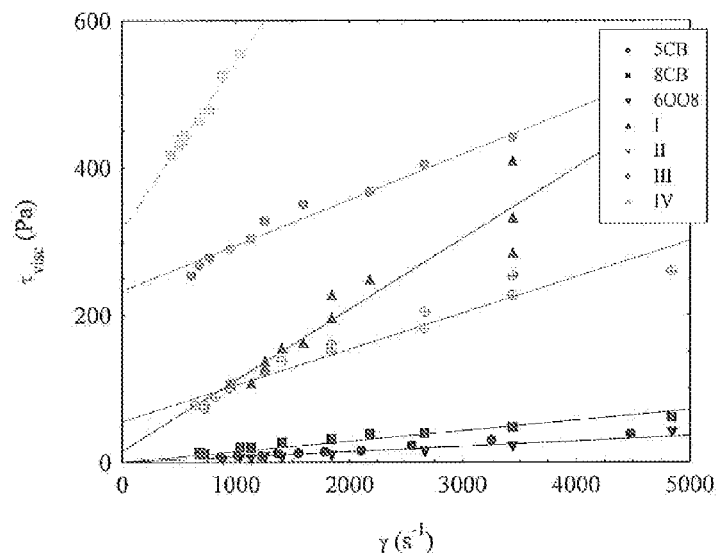
FIG. 10 shows measured shear rate dependence of the viscous stress for several nematic (calamitic and bent core) mesogens in the isotropic phase along with their fits of the apparent viscosity ($\eta^*$) shown in the equation. Three of the samples showed Newtonian flow behavior while four did not.
Figure 11:
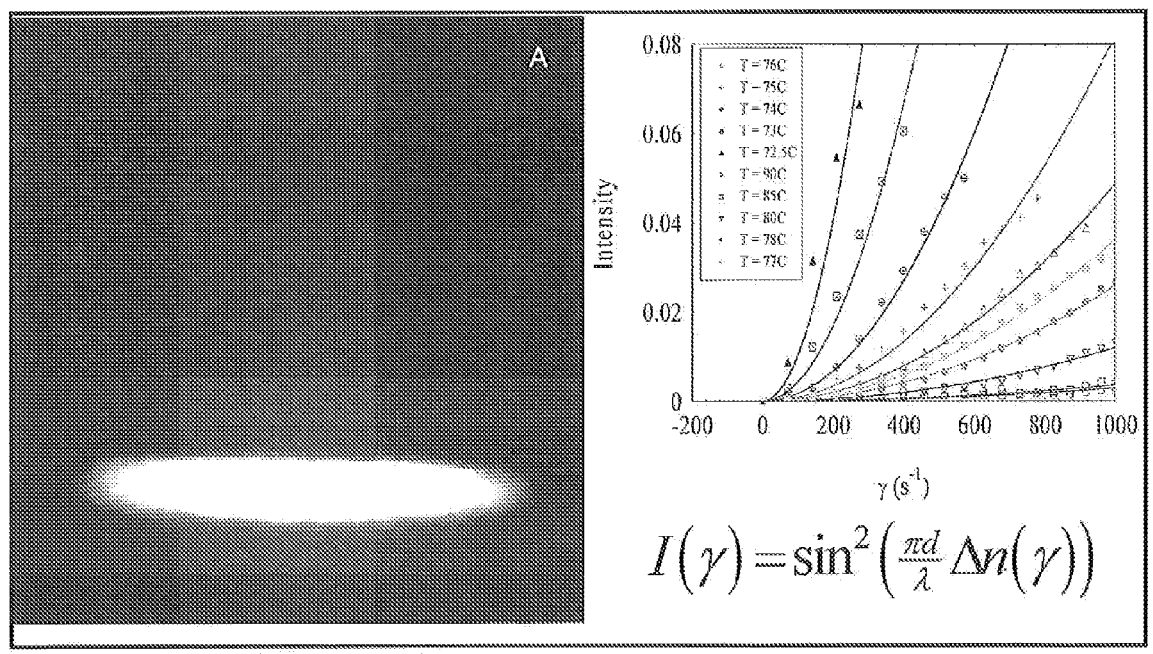
FIG. 11 shows the shear induced birefringence of material IV between crossed polarizers in the isotropic phase (76.3° C.) without shear (top left) and with shear (bottom left). Also shown is the graph of transmitted intensity versus shear rate at various temperatures above the nematic phase (top right), along with their best fits curves using the equation (bottom right) where the birefringence $\Delta n(\gamma)$ is proportional to the shear stress for low shear rates.

Finally, a comparison of the measured viscous stress of several nematic materials in the isotropic phase as a function of shear rate is set forth in FIG. 10.

Table 1 lists the names, chemical structures, and phase sequence under cooling for various materials. Both Newtonian and non-Newtonian behavior was seen by the non-zero extrapolated stress at zero shear rate for some of the samples. This is a clear indication of Bingham fluid behavior that occurs in many complex fluids such as foams.

Table 1: List of liquid crystal materials studied, their chemical structures, and their phase sequences

TABLE 1

| Name | Chemical Name | Phase Sequence (cooling) |
|---|---|---|
| 5CB | 4'-Pentyl-biphenyl-4-carbonitrile | Iso 35.3° C. Nem 24° C. Cr |
| 8CB | 4'-Octyl-bephenyl-4-carbonitrile | Iso 40.5° C. Nem 33.5° C. SmA 21.5° C. Cr |
| 6OO8 | 4-n-octyloxyphenyl 4-n-hexyloxybenzoate | Iso 87.7° C. Nem 46.2° C. SmC 37.6° C. Cr |
| I | 4,6-dichloro-1,3-phenylene-bis[4'-(7-octen-1-yloxy)-1,1'-biphenyl]4-carboxylate | Iso 94° C. Nem 60° C. Cr |
| II | 4,6-dichloro-1.3-phenylene-bis[4-(8-nonen-1-yloxy)-1,1'-biphenyl]4-carboxylate | Iso 86.8° C. Nem 50° C. Cr |
| III | 4-chloro-1,3-phenylene bis[4-decan-1-yloxy)benzoyloxy]benzoate | Iso 86.8° C. Nem 58° C. Cr |
| IV | 4-chloro-1,3-phenylene bis[4-(10-decen-1-yloxy)benzoloxy]benzoate | Iso 71.3° C. Nem 56° C. CR |

Optical Measurements

Another aspect of this measurement technique is the ability to couple optical measurement techniques to the force measurements. This is done by placing the device under a polarizing microscope where the polarizers were crossed. Below are two images of a droplet of material IV in the isotropic phase studied in this manner. The top left image is what the material looks like when no shear is applied, and the bottom left is the same droplet under shear. A clear flow birefringence effect which can be detected with a photodiode. This transmission effect is also clearly detectible with a photodiode as can be seen in top right of FIG. 11.

The nanoliter rheometer of the present invention was utilized to measure viscosities of four viscosity standards provided by an instrument company wherein the viscosities ranged over several orders of magnitude. The materials tested along with their extrapolated viscosities at 30° are set forth in Table 2.

TABLE 2

Viscosity Standard Chart

| Product Name | $\eta$ 2 30° C. (Pa s)* | Comments |
|---|---|---|
| N250 | 0.38 | Analysis Provided |
| N350 | 0.47 | Analysis Provided |
| N15000 | 31 | Analysis Provided |
| N18000 | 43 | Analysis Provided |

*Viscosities were obtained by extrapolating from data obtained from Cannon Instrument Company of State College, PA.

Several measurements related to calibration and property determination were performed. The results of the nanoliter rheometer were compared to the reported viscosity standards of the fluids as set forth in Table 2. All samples geometries and the description utilized are described herein above. All measurements were carried out at room temperature (20-25° C.) that was not controlled, so 2-5° C. range of variation of the temperatures was possible. Since the values used for comparison were measured at 30° C., the obtained measured values were expected somewhat larger and varied slightly due to variation of the temperatures.

Calibration Techniques

The parameters utilized to extract the background effects are listed below. These values were compared with a prior analysis before and after the one of the filaments broke and had to be repaired.

TABLE 3

Important Constants for Calculating Viscosity

| Property Name | From First Calibration | This Calibration Before Break | This Calibration After Break |
|---|---|---|---|
| $\delta$ | 0 µm $\leq \delta \leq$ 75 µm | 75 µm | 75 µm |
| $\phi_0$ | 75° | −105° | −105° |
| $\phi_1$ | 6° | 186° | 161° |
| $m_{\mathit{eff}}$ | 0/36 ± 0.04 mg | 0.35 mg | 0.15 mg |

Figure 12:
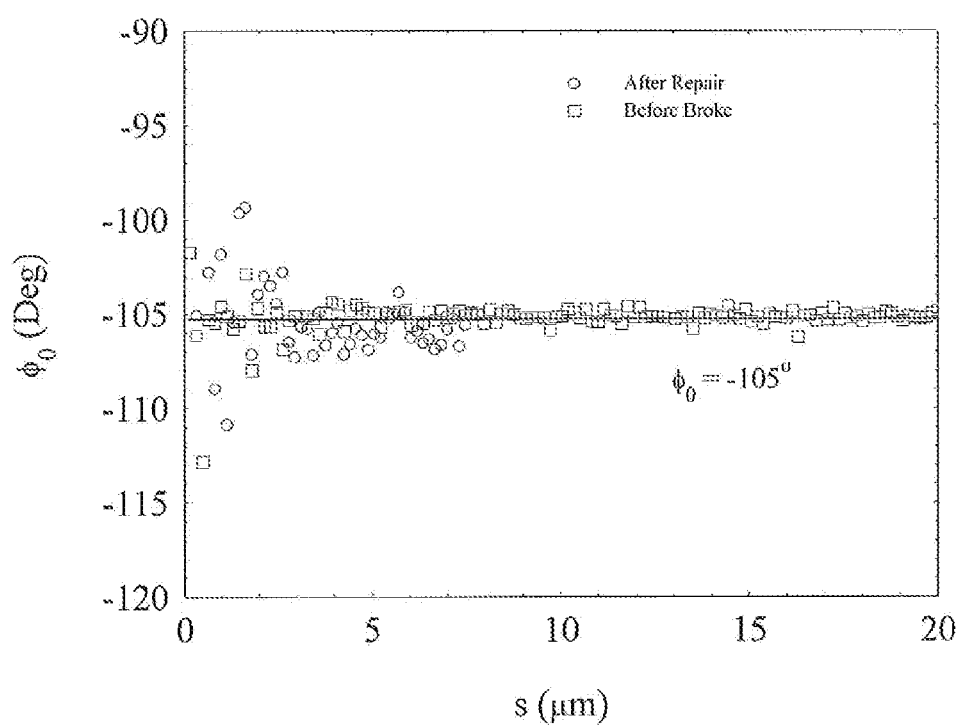
FIG. 12 shows the determination of the constant phase shift $\phi_0$ as a function of the speaker amplitude before and after the filament broke and was repaired.

Before the filament broke, phases $\phi_0$ and $\phi_1$ compared well to those previously studied except that they were out of phase by 180°, which occurred because the driving voltage was connected in reverse to speaker during resetting up the viscometer in a new lab. The parameter $\phi_0$ is determined as the phase difference between the voltage driving the speaker and the current measured on the piezo sensor attached to the stationary fiber when a solid material connects the fibers. This should depend only on the phase shift of the electronics and was not expected to change as the fibers, or glue connecting the fibers was changed. As seen in FIG. 12, they measured the same for two different fibers. On the other hand, the values of $m_{eff}$ and $\phi_1$ (which is the phase shift due to the inertial term $m_{eff}$) both changed after the filament broke and was changed. The value of the extrapolation length $\delta$, this should be the glass rod radius in order to obtain the correct viscosity values described in Table 3.

Results and Discussion

Figure 13:
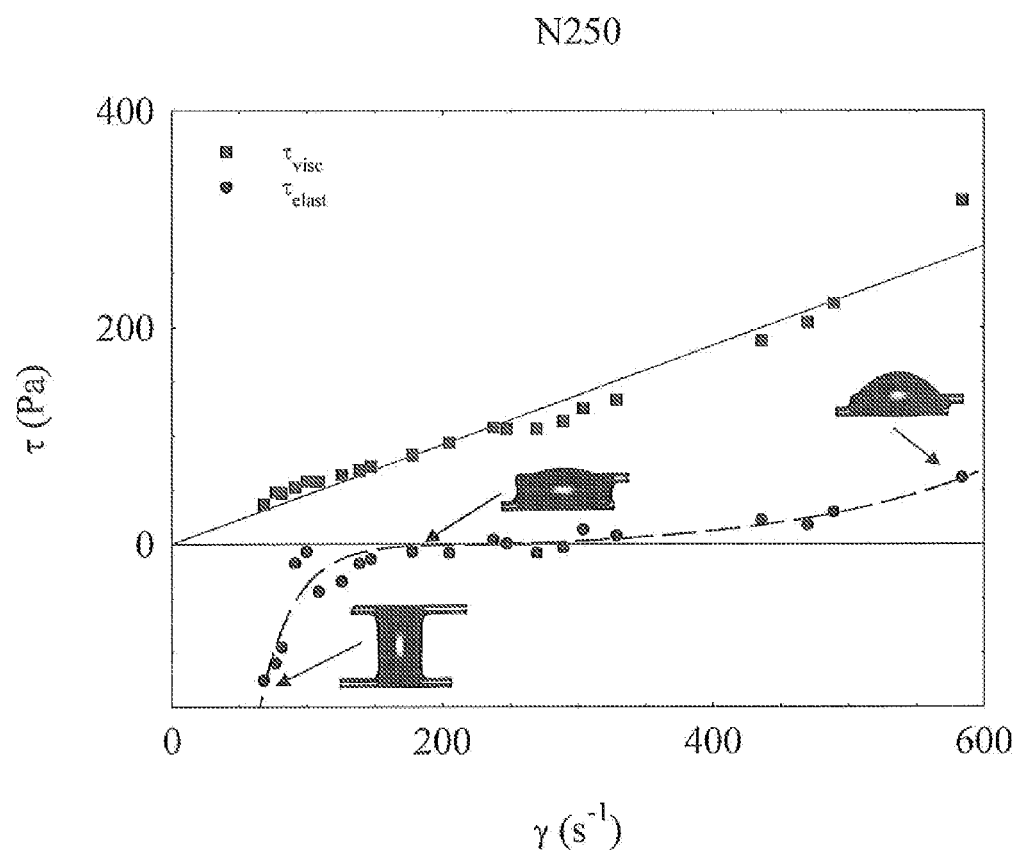
FIG. 13 shows the measured shear stress for the N250 sample as the distance between the filaments was varied.
Figure 14:
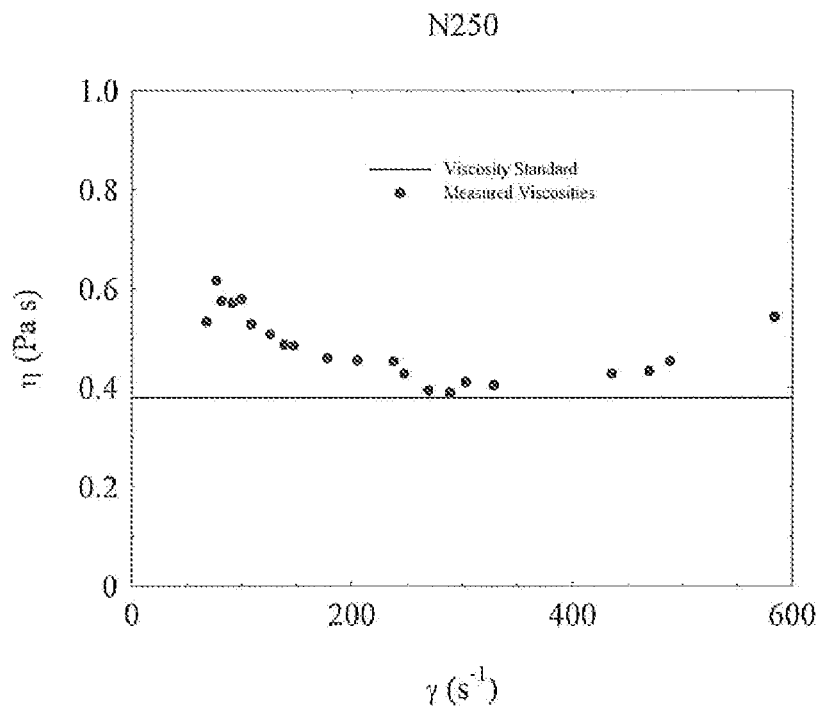
FIG. 14 shows the measured viscosity for N250 compared with the extrapolated value given in Table 2.

The effects of shear rate on the measured viscosity of the four samples will be discussed. In FIG. 13 the viscous and elastic shear stresses were measured using the methods described hereinabove. In FIG. 13, the shear rate was adjusted by varying the distance between the glass fibers at a constant amplitude and frequency (s=70 microns and f=130 Hz respectively). Example droplet geometries are shown at various points in the FIG. 13. It is seen that for the mid-range shear rates between 150-350 $s^{-1}$ the elastic shear stress is zero which is what was expected for these viscosity standards. However, at low shear rates and large shear rates the elastic shear stress differs from zero, which can be associated to effects outside the fluid. At low shear rates (large spacing), this difference is associated with decreases in sensitivity and is close to the Plateau-Rayleigh instability related to the effects of surface tension. At large shear rates (small distances) the difference is related to interactions between the rods due to slight misalignment and transverse vibration. It can be seen in FIG. 13 that this effect influences more the elastic stress than of the viscous one. The calculated viscosity from FIG. 13 is shown in FIG. 14 where good agreement to the expected value is indicated by the horizontal line. In particular, the viscosities match best in the region between 200-350 $s^{-1}$ for the samples with moderate viscosities which coincides well with the region in FIG. 13 where the elastic stress is near zero. For the highly viscous materials, the most accurate results can be observed at lower (100-200 $s^{-1}$) shear rates, because the signal is still large at lower rates, but at high shear rates their interactions with the rods seem to be more pronounced.

Figure 15:
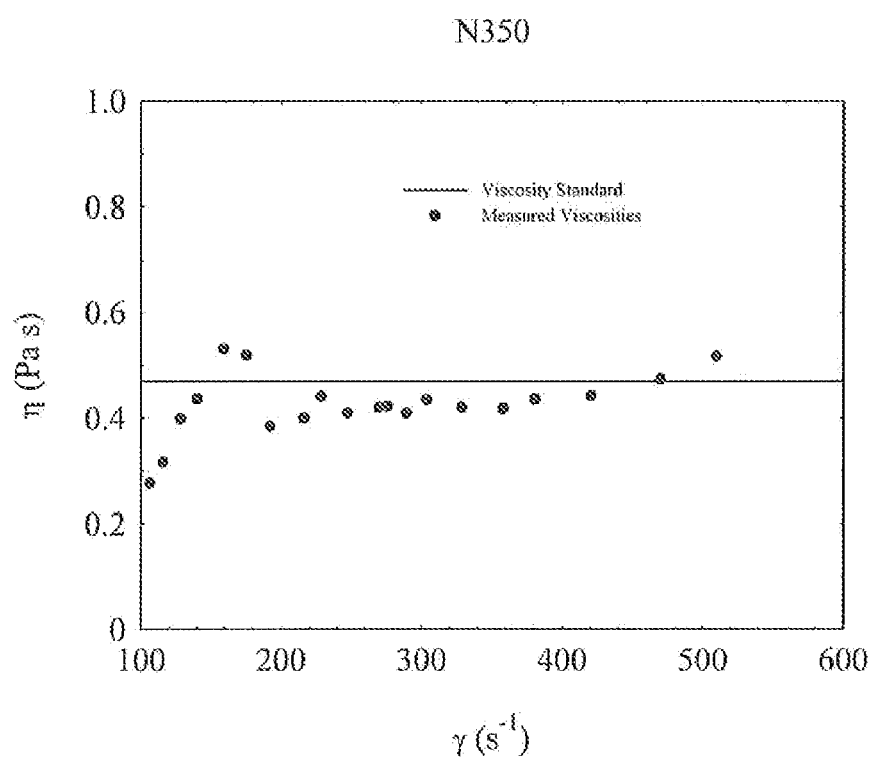
FIG. 15 shows the measured viscosity for N350 compared with the extrapolated value given in Table 2.
Figure 16:
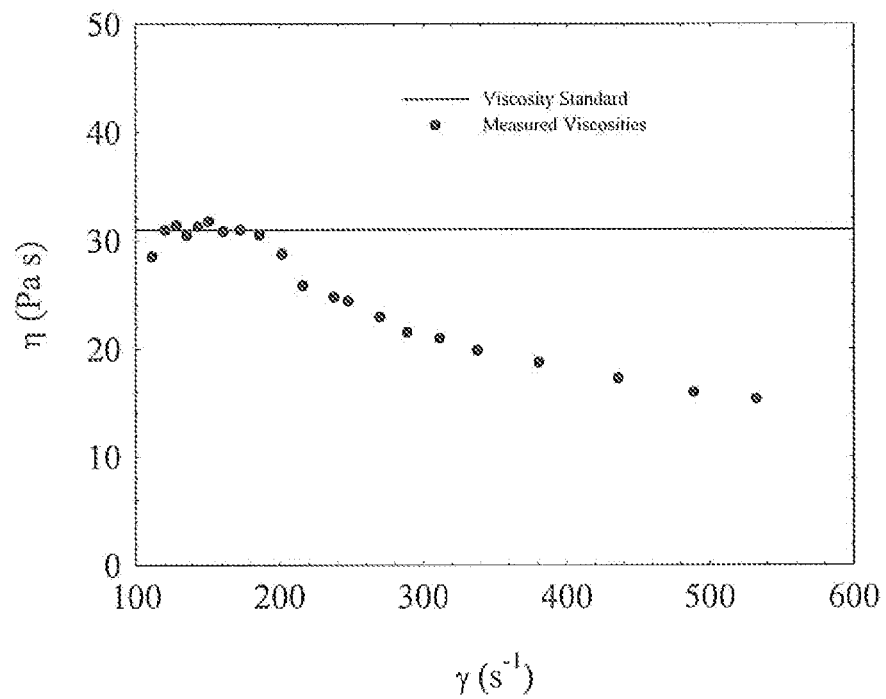
FIG. 16 shows the measured viscosity for N15000 compared with the extrapolated value given in Tale 2.
Figure 17:
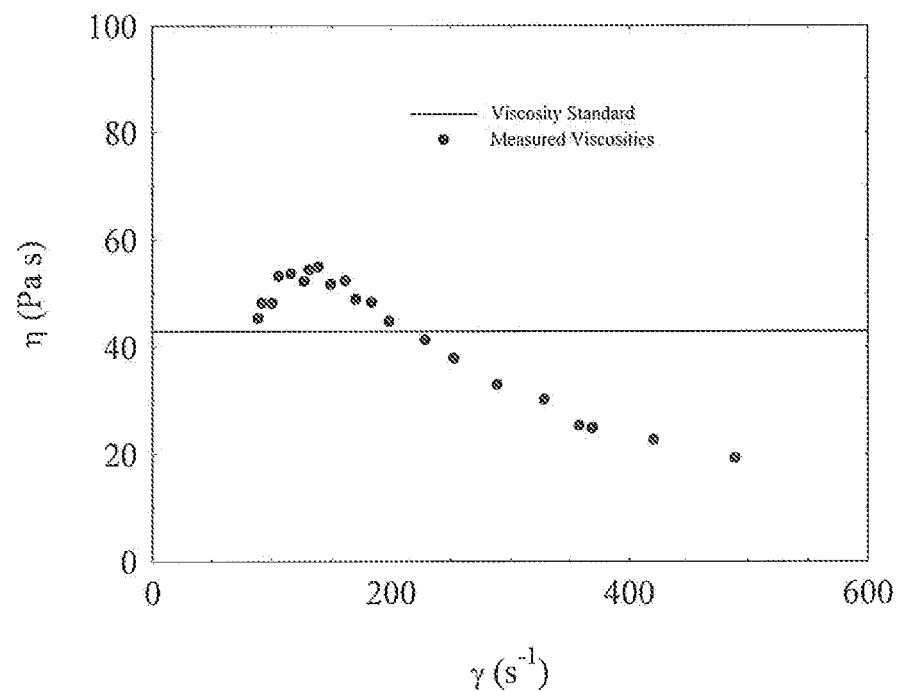
FIG. 17 shows the measured viscosity for N18000 compared with the extrapolated value given in Table 2.

Similar viscosity measurements are shown in FIGS. 15-17 for the samples N350, N15000, and N18000 respectfully. All samples showed similar measured values as compared to the reported vales in Table 2. The averages of these measurements are calculated in the 100-200 $s^{-1}$ rates for the N250 and N350 samples, and in the 100-200$^{-1}$ range for the N15000 and N18000 samples. They and the average percent differences, are shown in Table 4. All of the samples have a percent difference less than 12%.

TABLE 4

Comparisons of measured viscosities to the viscosity standards with % difference

| Sample | Reported Value | Average Value | Average % Diff. |
|---|---|---|---|
| N250 | 0.38 Pas | 0.42 ± 0.04 Pas | 10.6% |
| N350 | 0.47 Pas | 0.42 ± 0.05 Pas | 11.0% |
| N15000 | 31 Pas | 30.5 ± 2 Pas | 1.6% |
| N18000 | 43 Pas | 49 ± 6 Pas | 11.2% |

It is also seen that the most viscous samples N15000 and N18000 show a clear shear thinning effect above a shear rate of 200 $s^{-1}$.

Finally, in order to study the reproducibility of these results, tests were run wherein the fiber spacing was approximately constant but the fluid between the fibers was changed and measured by using capillary action. One result of this method was that it was difficult to control the spacing (i.e. the shear rate). The results of these measurements are shown in Table 5. The results for these measurements are comparable to those from the previous studies. The tabulated values for all of the measured data are listed in the following appendixes.

TABLE 5

Comparisons of measured viscosities to the viscosity standards with % difference

| Sample | Reported Value | Average Value | Average % Diff |
|---|---|---|---|
| N250 | 0.38 Pas | 0.3861 ± 0.03 Pas | 1.8% |
| N350 | 0.47 Pas | 0.57 ± 0.05 Pas | 19.6% |
| N15000 | 31 Pas | 28 ± 4 Pas | 9.5% |
| N18000 | 43 Pas | 48 ± 4 Pas | 10.5% |

Note that for N350 the reproducibility measurements were carried out at 300 $s^{-1}$ which is over the optimum rates, causing the relatively large error.

The data utilized to plot FIGS. 14 through 17 are set forth below in Tables 6, 7, 8, and 9.

Graph 11: N250

| Shear Rate ($s^{-1}$) | Viscosity (Pa s) |
|---|---|
| 5.84E+02 | 5.42E−01 |
| 4.89E+02 | 4.53E−01 |
| 4.70E+02 | 4.33E−01 |
| 4.36E+02 | 4.28E−01 |
| 3.29E+02 | 4.04E−01 |
| 3.04E+02 | 4.11E−01 |
| 2.89E+02 | 3.90E−01 |
| 2.70E+02 | 3.94E−01 |
| 2.48E+02 | 4.28E−01 |
| 2.38E+02 | 4.52E−01 |
| 2.05E+02 | 4.55E−01 |
| 1.78E+02 | 4.59E−01 |
| 1.47E+02 | 4.84E−01 |
| 1.39E+02 | 4.86E−01 |
| 1.26E+02 | 5.07E−01 |
| 1.09E+02 | 5.28E−01 |
| 9.98E+01 | 5.78E−01 |
| 9.15E+01 | 5.70E−01 |
| 8.15E+01 | 5.74E−01 |
| 7.69E+01 | 6.15E−01 |
| 6.82E+01 | 5.33E−01 |

Graph 12: N350

| Shear Rate ($s^{-1}$) | Viscosity (Pa s) |
|---|---|
| 6.47E+02 | 7.31E−01 |
| 5.10E+02 | 5.16E−01 |
| 4.70E+02 | 4.73E−01 |
| 4.21E+02 | 4.42E−01 |
| 3.81E+02 | 4.35E−01 |
| 3.58E+02 | 4.17E−01 |
| 3.29E+02 | 4.19E−01 |
| 3.04E+02 | 4.34E−01 |
| 2.89E+02 | 4.09E−01 |
| 2.76E+02 | 4.21E−01 |
| 2.70E+02 | 4.20E−01 |
| 2.48E+02 | 4.09E−01 |
| 2.29E+02 | 4.40E−01 |
| 2.16E+02 | 3.99E−01 |
| 1.92E+02 | 3.84E−01 |
| 1.75E+02 | 5.18E−01 |
| 1.59E+02 | 5.31E−01 |
| 1.41E+02 | 4.36E−01 |

-continued

| Graph 12: N350 | |
| --- | --- |
| Shear Rate (s$^{-1}$) | Viscosity (Pa s) |
| 1.29E+02 | 3.98E−01 |
| 1.16E+02 | 3.17E−01 |
| 1.07E+02 | 2.77E−01 |

| Graph 13: N15000 | |
| --- | --- |
| Shear Rate (s$^{-1}$) | Viscosity (Pa s) |
| 5.33E+02 | 1.53E+01 |
| 4.89E+02 | 1.59E+01 |
| 4.36E+02 | 1.73E+01 |
| 3.81E+02 | 1.87E+01 |
| 3.38E+02 | 1.98E+01 |
| 3.12E+02 | 2.09E+01 |
| 2.89E+02 | 2.15E+01 |
| 2.70E+02 | 2.29E+01 |
| 2.48E+02 | 2.44E+01 |
| 2.38E+02 | 2.47E+01 |
| 2.16E+02 | 2.58E+01 |
| 2.02E+02 | 2.87E+01 |
| 1.86E+02 | 3.05E+01 |
| 1.73E+02 | 3.09E+01 |
| 1.61E+02 | 3.08E+01 |
| 1.51E+02 | 3.17E+01 |
| 1.44E+02 | 3.13E+01 |
| 1.36E+02 | 3.04E+01 |
| 1.29E+02 | 3.13E+01 |
| 1.21E+02 | 3.09E+01 |
| 1.12E+02 | 2.85E+01 |

| Graph 14: N18000 | |
| --- | --- |
| Shear Rate (s$^{-1}$) | Viscosity (Pa s) |
| 4.89E+02 | 1.93E+01 |
| 4.21E+02 | 2.26E+01 |
| 3.69E+02 | 2.48E+01 |
| 3.58E+02 | 2.53E+01 |
| 3.29E+02 | 3.01E+01 |
| 2.89E+02 | 3.29E+01 |
| 2.539E+02 | 3.78E+01 |
| 2.294E+02 | 4.13E+01 |
| 1.99E+02 | 4.489E+01 |
| 1.83E+02 | 4.83E+01 |
| 1.70E+02 | 4.89E+01 |
| 1.61E+02 | 5.24E+01 |
| 1.49E+02 | 5.17E+01 |
| 1.39E+02 | 5.50E+01 |
| 1.31E+02 | 5.44E+01 |
| 1.27E+02 | 5.23E+01 |
| 1.16E+02 | 5.37E+01 |
| 1.06E+02 | 5.32E+01 |
| 1.01E+02 | 4.82E+01 |
| 9.22E+01 | 4.82E+01 |
| 8.88E+01 | 4.54E+01 |

SUMMARY

The various supplied viscosity standards were analyzed. It was shown that the viscosities could be determined within a 12% difference from the actual known values. Furthermore, it was also shown that similar results could be obtained by replacing the droplets between each measurement in an attempt to probe the reproducibility of the technique.

In summary, a description of a nanoliter rheometer for measuring the viscoelastic behavior of Non-Newtonian fluids using very small amounts of material (~10 nL) has been set forth. Techniques have been developed for the rheometer that allows easy calibration and calculation of viscosity. Unlike many methods that require larger amounts of material, this method directly measures the force and phase shift of an applied stress, resulting in the ability to expand the rheometer beyond simple viscosity measurements (a property not capable in almost all small volume viscometers). This method also allows one to reduce the sensitivity of rheometer device by adjusting with the applied frequency, contact area, displacement amplitude, etc. Furthermore, resonance measurements can be used along with an impendence analyzer to determine viscoelastic properties at resonant frequencies, a region not accessible with the lock-in techniques. This duel mode operation allows one to perform a wide variety of viscoelastic measurements. It has also been shown how optical properties, such as flow birefringence can be measured with the rheometer via the use of a microscope while applying shear.

While in accordance with the patent statutes the best mode and preferred embodiment have been set forth, the scope of the invention is not intended to be limited thereto, but only by the scope of the attached claims.

What is claimed is:

1. A nanoliter rheometer, comprising:
   a thin motion fiber and a thin substantially stationary fiber,
   the ends of said motion fiber and said stationary fiber being opposed to each other and are in close proximity and substantially parallel to each other; or the ends of said motion fiber and said stationary fiber generally have a common axis and are in close proximity to each other;
   said ends of said motion fiber and said substantially stationary fiber capable of retaining a droplet of fluid therebetween;
   a drive system connected to and for imparting motion to said motion fiber; and
   a transferred force measurement device connected to said stationary fiber and capable of measuring the force imparted to said substantially stationary fiber by said motion fiber through said fluid.

2. The nanoliter rheometer of claim 1, wherein said motion fiber and said stationary fiber, independently, have a diameter of from about 50 microns to about 1 millimeter, wherein said nanoliter sized fluid is either a Newtonian fluid or a non-Newtonian fluid; and wherein the amount of said fluid is from about 5 to about 200 nanoliters.

3. The nanoliter rheometer of claim 2, including a substantially enclosed chamber, wherein said end of said motion fiber and said stationary fiber, independently, are located in said chamber; wherein said motion fiber and said stationary fiber, independently, is plastic, glass, a metal, a non-metal, or any combination thereof; and wherein said fiber ends extend in an x direction and overlap in a y and/or z direction and said stationary fiber is approximately located from about 1 micron to about 1 millimeter from said motion fiber; or wherein said fiber ends have a common axis and the gap distance between said ends is from about 1 to about 100 microns when said motion fiber is closest to said stationary fiber.

4. The nanoliter rheometer of claim 3, wherein the amount of said fluid is from about 10 to about 100 nanoliters; wherein said drive system comprises a transducer; wherein said transfer force measurement device comprises a piezoelectric crystal or an inductance capacitance resistance meter, and wherein said transferred force measurement device is located opposite to said drive system.

5. The nanoliter rheometer of claim 4, wherein said motion fiber diameter and said stationary fiber diameter, independently, is from about 100 to about 500 microns; wherein said motion fiber and said stationary fiber, independently, is a thermoplastic, or a thermoset, or any combination thereof, a metal comprising steel, aluminum, copper, brass, or titanium, or any combination thereof, a non-metal fiber comprising boron, or carbon, or a combination thereof, or a glass; wherein said transducer comprises a motor, or a speaker, for oscillating said motion fiber; and wherein said gap distance between the ends of said fibers when said fibers have a common axis is from about 10 to about 75 microns when said motion fiber is closest to said stationary fiber.

6. The nanoliter rheometer of claim 5, wherein the cross-section of said motion fiber and said stationary fiber is circular; wherein the end of said motion fiber is generally located either horizontally in front of or horizontally in back of said stationary fiber; wherein the said distance between said stationary fiber and said motion fiber is from about 10 to about 200 microns; and wherein a drive support system can move said motion fiber laterally with respect to said stationary fiber.

7. The nanoliter rheometer of claim 6, wherein said fluid comprises a liquid crystal, a biological substance, an elastomer, a gel, a polymer solution, a polymer, a colloidal suspension, a foam, a fluid mixture, a nanoparticle solution, or any combination thereof.

8. A nanoliter rheometer of claim 5, wherein said nanoliter rheometer is capable of measuring the viscosity or elasticity of a nano-size fluid of from about 10 to about 100 nanoliters comprising a DNA solution, a protein solution, or a solution of living cells.

9. The nanoliter rheometer of claim 3, wherein said fluid comprises a liquid crystal, a biological substance, an elastomer, a gel, a polymer solution, a polymer, a colloidal suspension, a foam, a fluid mixture, a nanoparticle solution, or any combination thereof.

10. The nanoliter rheometer of claim 1, wherein said fluid comprises a liquid crystal, a biological substance, an elastomer, a gel, a polymer solution, a polymer, a colloidal suspension, a foam, a fluid mixture, a nanoparticle solution, or any combination thereof.

11. The nanoliter rheometer of claim 1, wherein said nanoliter rheometer is capable of measuring the viscosity or elasticity of a nano-size fluid of from about 5 to about 200 nanoliters comprising a DNA solution, a protein solution, or a solution of living cells.

12. A process for measuring a force transferred through a nano-size fluid, comprising the steps of:

utilizing a nanoliter rheometer, said rheometer comprising:
a thin motion fiber and a thin substantially stationary fiber,
the ends of said motion fiber and said stationary fiber being in close proximity and substantially parallel to each other; or the ends of said motion fiber and said stationary fiber generally have a common axis;
said ends of said motion fiber and said substantially stationary fiber capable of retaining a small nanoliter sized fluid therebetween;
a drive system connected to and for imparting motion to said motion fiber; and
a transferred force measurement device connected to said stationary fiber and capable of measuring the force imparted to said substantially stationary fiber by said motion fiber through said fluid;
placing a nanoliter size amount of a Newtonian fluid or a non-Newtonian fluid between the ends of said motion fiber and said stationary fiber;
oscillating said motion fiber and measuring the force transferred by said oscillating fiber through said nanoliter size fluid by said transferred force measurement device.

13. The process according to claim 12, wherein said motion fiber and said stationary fiber, independently, have a diameter of from about 50 microns to about 1 millimeter; and wherein said amount of said nanoliter sized fluid is from about 5 to about 200 nanoliters.

14. The process according to claim 13, wherein the amount of said fluid is from about 10 to about 100 nanoliters; wherein said drive system comprises a transducer; and wherein said transfer force measurement device comprises a piezoelectric crystal or an inductance capacitance resistance meter.

15. The process according to claim 14, wherein said motion fiber diameter and said stationary fiber diameter, independently, is from about 100 to about 500 microns; and wherein the cross-section of said motion fiber and said stationary fiber is circular; wherein the end of said motion fiber is generally located either horizontally in front of or horizontally in back of said stationary fiber; and wherein the said distance between said stationary fiber and said motion fiber is from about 10 to about 200 microns.

16. The process according to claim 12, wherein said motion fiber and said stationary fiber, independently, are plastic, glass, a metal, a non-metal, or any combination thereof; and wherein said fluid comprises a liquid crystal, a biological substance, an elastomer, a gel, a polymer solution, a polymer, a colloidal suspension, a foam, a fluid mixture, a nanoparticle solution, or any combination thereof.

* * * * *